(12) United States Patent
Dreyfuss

(10) Patent No.: US 9,301,745 B2
(45) Date of Patent: Apr. 5, 2016

(54) KNOTLESS SUTURE CONSTRUCTS

(75) Inventor: Peter J. Dreyfuss, Naples, FL (US)

(73) Assignee: Arthrex, Inc., Naples, FL (US)

( * ) Notice: Subject to any disclaimer, the term of this patent is extended or adjusted under 35 U.S.C. 154(b) by 503 days.

(21) Appl. No.: 13/553,230

(22) Filed: Jul. 19, 2012

(65) Prior Publication Data

US 2013/0023928 A1 Jan. 24, 2013

Related U.S. Application Data

(60) Provisional application No. 61/510,341, filed on Jul. 21, 2011.

(51) Int. Cl.
*A61B 17/04* (2006.01)
*A61B 17/06* (2006.01)

(52) U.S. Cl.
CPC ......... *A61B 17/0401* (2013.01); *A61B 17/0469* (2013.01); *A61B 17/06166* (2013.01); *A61B 2017/044* (2013.01); *A61B 2017/0409* (2013.01); *A61B 2017/0414* (2013.01); *A61B 2017/0496* (2013.01)

(58) Field of Classification Search
CPC ................ A61B 17/0401; A61B 17/06166; A61B 17/0469; A61B 2017/0409; A61B 2017/044; A61B 2017/0496; A61B 2017/0414
USPC ..................... 606/103, 144–150, 228–233
See application file for complete search history.

(56) References Cited

U.S. PATENT DOCUMENTS

| | | | |
|---|---|---|---|
| 3,176,316 A | 4/1965 | Bodell | |
| 4,187,558 A | 2/1980 | Dahlen et al. | |
| 4,301,551 A | 11/1981 | Dore et al. | |
| 4,400,833 A | 8/1983 | Kurland | |
| 4,776,851 A | 10/1988 | Bruchman et al. | |
| 4,790,850 A | 12/1988 | Dunn et al. | |
| 4,792,336 A | 12/1988 | Hlavacek et al. | |
| 4,851,005 A | 7/1989 | Hunt et al. | |
| 4,863,471 A | 9/1989 | Mansat | |
| 4,917,700 A | 4/1990 | Aikins | |
| 4,932,972 A | 6/1990 | Dunn et al. | |
| 5,024,669 A | 6/1991 | Peterson et al. | |
| 5,026,398 A | 6/1991 | May et al. | |
| 5,129,902 A | 7/1992 | Goble et al. | |
| 5,171,274 A | 12/1992 | Fluckiger et al. | |
| 5,211,647 A | 5/1993 | Schmieding | |
| 5,217,495 A | 6/1993 | Kaplan et al. | |
| 5,263,984 A | 11/1993 | Li et al. | |
| 5,266,075 A | 11/1993 | Clark et al. | |
| 5,306,301 A | 4/1994 | Graf et al. | |
| 5,320,626 A | 6/1994 | Schmieding | |

(Continued)

FOREIGN PATENT DOCUMENTS

| | | | |
|---|---|---|---|
| EP | 0 440 991 A1 | 8/1991 | |
| EP | 1 108 401 A1 | 6/2001 | |

(Continued)

*Primary Examiner* — David C Eastwood
(74) *Attorney, Agent, or Firm* — Blank Rome LLP

(57) ABSTRACT

Systems and methods for soft tissue to bone repairs, without knot tying. The soft tissue repair systems include self-cinching constructs with at least one splice area, a turning loop (turning eyelet), a fixed end and a tensioning limb. The eyelet is fixed and is created into the suture splice by splicing or knotting, or by other known methods in the art. The eyelet is configured to redirect the tensioning of the construct (the force of tensioning).

5 Claims, 8 Drawing Sheets

(56) References Cited

U.S. PATENT DOCUMENTS

| | | | |
|---|---|---|---|
| 5,397,357 A | 3/1995 | Schmieding et al. | |
| 5,562,669 A | 10/1996 | McGuire | |
| 5,575,819 A | 11/1996 | Amis | |
| 5,628,756 A | 5/1997 | Barker et al. | |
| 5,643,266 A | 7/1997 | Li | |
| 5,645,588 A | 7/1997 | Graf et al. | |
| 5,931,869 A | 8/1999 | Boucher et al. | |
| 5,961,520 A | 10/1999 | Beck et al. | |
| 5,964,764 A | 10/1999 | West, Jr. et al. | |
| 6,056,752 A | 5/2000 | Roger | |
| 6,099,530 A | 8/2000 | Simonian et al. | |
| 6,099,568 A | 8/2000 | Simonian et al. | |
| 6,110,207 A | 8/2000 | Eichhorn et al. | |
| 6,159,234 A | 12/2000 | Bonutti et al. | |
| 6,193,754 B1 | 2/2001 | Seedhom | |
| 6,203,572 B1 | 3/2001 | Johnson et al. | |
| 6,283,996 B1 | 9/2001 | Chervitz et al. | |
| 6,296,659 B1 | 10/2001 | Foerster | |
| 6,325,804 B1 | 12/2001 | Wenstrom et al. | |
| 6,517,578 B2 | 2/2003 | Hein | |
| 6,533,802 B2 | 3/2003 | Bojarski et al. | |
| 7,097,654 B1 | 8/2006 | Freedland | |
| 7,494,506 B2 | 2/2009 | Brulez et al. | |
| 7,686,838 B2 | 3/2010 | Wolf et al. | |
| 7,749,250 B2 | 7/2010 | Stone et al. | |
| 7,776,039 B2 | 8/2010 | Bernstein et al. | |
| 7,819,898 B2 | 10/2010 | Stone et al. | |
| 7,828,855 B2 | 11/2010 | Ellis et al. | |
| 7,875,057 B2 | 1/2011 | Cook et al. | |
| 7,905,903 B2 | 3/2011 | Stone et al. | |
| 7,914,539 B2 | 3/2011 | Stone et al. | |
| 8,109,965 B2 | 2/2012 | Stone et al. | |
| 8,118,836 B2 | 2/2012 | Denham et al. | |
| 8,162,997 B2 | 4/2012 | Struhl | |
| 8,206,446 B1 | 6/2012 | Montgomery | |
| 8,231,654 B2 | 7/2012 | Kaiser et al. | |
| 2001/0041938 A1* | 11/2001 | Hein | 623/13.13 |
| 2002/0161439 A1 | 10/2002 | Strobel et al. | |
| 2003/0114929 A1 | 6/2003 | Knudsen et al. | |
| 2004/0015171 A1 | 1/2004 | Bojarski et al. | |
| 2004/0059415 A1 | 3/2004 | Schmieding | |
| 2004/0073306 A1 | 4/2004 | Eichhorn et al. | |
| 2004/0093031 A1* | 5/2004 | Burkhart et al. | 606/232 |
| 2004/0243235 A1 | 12/2004 | Goh et al. | |
| 2004/0267360 A1 | 12/2004 | Huber | |
| 2005/0004670 A1 | 1/2005 | Gebhardt et al. | |
| 2005/0033363 A1 | 2/2005 | Bojarski et al. | |
| 2005/0065533 A1 | 3/2005 | Magen et al. | |
| 2005/0070906 A1 | 3/2005 | Clark et al. | |
| 2005/0137704 A1 | 6/2005 | Steenlage | |
| 2005/0149187 A1 | 7/2005 | Clark et al. | |
| 2005/0171603 A1 | 8/2005 | Justin et al. | |
| 2005/0203623 A1 | 9/2005 | Steiner et al. | |
| 2005/0245932 A1* | 11/2005 | Fanton et al. | 606/72 |
| 2005/0261766 A1 | 11/2005 | Chervitz et al. | |
| 2005/0267479 A1* | 12/2005 | Morgan et al. | 606/73 |
| 2006/0067971 A1 | 3/2006 | Story et al. | |
| 2006/0095130 A1 | 5/2006 | Caborn et al. | |
| 2006/0142769 A1 | 6/2006 | Collette | |
| 2006/0259076 A1* | 11/2006 | Burkhart et al. | 606/228 |
| 2006/0265064 A1 | 11/2006 | Re et al. | |
| 2007/0021839 A1 | 1/2007 | Lowe | |
| 2007/0083236 A1 | 4/2007 | Sikora et al. | |
| 2007/0118217 A1 | 5/2007 | Brulez et al. | |
| 2007/0135843 A1* | 6/2007 | Burkhart | 606/232 |
| 2007/0162123 A1 | 7/2007 | Whittaker et al. | |
| 2007/0162125 A1 | 7/2007 | LeBeau et al. | |
| 2007/0179531 A1 | 8/2007 | Thornes | |
| 2007/0191849 A1* | 8/2007 | ElAttrache et al. | 606/72 |
| 2007/0225805 A1 | 9/2007 | Schmieding | |
| 2007/0239209 A1* | 10/2007 | Fallman | 606/232 |
| 2007/0239275 A1 | 10/2007 | Willobee | |
| 2007/0250163 A1 | 10/2007 | Cassani | |
| 2007/0270857 A1 | 11/2007 | Lombardo et al. | |
| 2008/0046009 A1 | 2/2008 | Albertorio et al. | |
| 2008/0177302 A1 | 7/2008 | Shurnas | |
| 2008/0188935 A1 | 8/2008 | Saylor et al. | |
| 2008/0188936 A1 | 8/2008 | Ball et al. | |
| 2008/0208252 A1 | 8/2008 | Holmes | |
| 2008/0215150 A1 | 9/2008 | Koob et al. | |
| 2008/0228271 A1 | 9/2008 | Stone et al. | |
| 2008/0234819 A1 | 9/2008 | Schmieding et al. | |
| 2008/0243248 A1 | 10/2008 | Stone et al. | |
| 2008/0262544 A1* | 10/2008 | Burkhart | 606/232 |
| 2008/0275553 A1 | 11/2008 | Wolf et al. | |
| 2008/0275554 A1 | 11/2008 | Iannarone et al. | |
| 2008/0300683 A1 | 12/2008 | Altman et al. | |
| 2008/0312689 A1 | 12/2008 | Denham et al. | |
| 2009/0018654 A1 | 1/2009 | Schmieding et al. | |
| 2009/0030516 A1 | 1/2009 | Imbert | |
| 2009/0054982 A1 | 2/2009 | Cimino | |
| 2009/0062854 A1 | 3/2009 | Kaiser et al. | |
| 2009/0082805 A1 | 3/2009 | Kaiser et al. | |
| 2009/0138042 A1* | 5/2009 | Thal | 606/232 |
| 2009/0187244 A1 | 7/2009 | Dross | |
| 2009/0216326 A1 | 8/2009 | Hirpara et al. | |
| 2009/0228017 A1 | 9/2009 | Collins | |
| 2009/0234451 A1 | 9/2009 | Manderson | |
| 2009/0265003 A1 | 10/2009 | Re et al. | |
| 2009/0275950 A1 | 11/2009 | Sterrett et al. | |
| 2009/0306711 A1* | 12/2009 | Stone et al. | 606/232 |
| 2009/0306776 A1 | 12/2009 | Murray | |
| 2009/0306784 A1 | 12/2009 | Blum | |
| 2009/0312776 A1 | 12/2009 | Kaiser et al. | |
| 2010/0049258 A1 | 2/2010 | Dougherty | |
| 2010/0049319 A1 | 2/2010 | Dougherty | |
| 2010/0077718 A1* | 4/2010 | Wienke et al. | 59/84 |
| 2010/0100182 A1 | 4/2010 | Barnes et al. | |
| 2010/0145384 A1 | 6/2010 | Stone et al. | |
| 2010/0145448 A1 | 6/2010 | Montes De Oca Balderas et al. | |
| 2010/0160962 A1* | 6/2010 | Dreyfuss et al. | 606/228 |
| 2010/0211075 A1 | 8/2010 | Stone | |
| 2010/0211173 A1 | 8/2010 | Bardos et al. | |
| 2010/0249930 A1 | 9/2010 | Myers | |
| 2010/0268273 A1 | 10/2010 | Albertorio et al. | |
| 2010/0268275 A1 | 10/2010 | Stone et al. | |
| 2010/0274355 A1 | 10/2010 | McGuire et al. | |
| 2010/0274356 A1 | 10/2010 | Fening et al. | |
| 2010/0292792 A1 | 11/2010 | Stone et al. | |
| 2010/0305709 A1 | 12/2010 | Metzger et al. | |
| 2010/0312341 A1 | 12/2010 | Kaiser et al. | |
| 2010/0318188 A1 | 12/2010 | Linares | |
| 2010/0324676 A1 | 12/2010 | Albertorio et al. | |
| 2010/0331975 A1 | 12/2010 | Nissan et al. | |
| 2011/0040380 A1 | 2/2011 | Schmieding et al. | |
| 2011/0046734 A1 | 2/2011 | Tobis et al. | |
| 2011/0054609 A1 | 3/2011 | Cook et al. | |
| 2011/0087284 A1* | 4/2011 | Stone et al. | 606/232 |
| 2011/0098727 A1 | 4/2011 | Kaiser et al. | |
| 2011/0112640 A1 | 5/2011 | Amis et al. | |
| 2011/0112641 A1 | 5/2011 | Justin et al. | |
| 2011/0118838 A1 | 5/2011 | Delli-Santi et al. | |
| 2011/0137416 A1 | 6/2011 | Myers | |
| 2011/0184227 A1 | 7/2011 | Altman et al. | |
| 2011/0196432 A1 | 8/2011 | Griffis, III | |
| 2011/0196490 A1 | 8/2011 | Gadikota et al. | |
| 2011/0218625 A1 | 9/2011 | Berelsman et al. | |
| 2011/0238179 A1 | 9/2011 | Laurencin et al. | |
| 2011/0270278 A1 | 11/2011 | Overes et al. | |
| 2011/0276137 A1 | 11/2011 | Seedhom et al. | |
| 2011/0288635 A1 | 11/2011 | Miller et al. | |
| 2011/0301707 A1 | 12/2011 | Buskirk et al. | |
| 2011/0301708 A1 | 12/2011 | Stone et al. | |
| 2012/0046746 A1 | 2/2012 | Konicek | |
| 2012/0046747 A1 | 2/2012 | Justin et al. | |
| 2012/0053630 A1 | 3/2012 | Denham et al. | |
| 2012/0065679 A1* | 3/2012 | Cauldwell et al. | 606/232 |
| 2012/0065732 A1 | 3/2012 | Roller et al. | |
| 2012/0071896 A1* | 3/2012 | Ferree | 606/139 |
| 2012/0089143 A1 | 4/2012 | Martin et al. | |
| 2012/0109299 A1 | 5/2012 | Li et al. | |
| 2012/0123474 A1 | 5/2012 | Zajac et al. | |
| 2012/0123541 A1 | 5/2012 | Albertorio et al. | |
| 2012/0150297 A1 | 6/2012 | Denham et al. | |

(56) References Cited

U.S. PATENT DOCUMENTS

| | | |
|---|---|---|
| 2012/0165938 A1 | 6/2012 | Denham et al. |
| 2012/0197271 A1 | 8/2012 | Astorino et al. |
| 2012/0296345 A1 | 11/2012 | Wack et al. |
| 2013/0023929 A1 | 1/2013 | Sullivan et al. |

FOREIGN PATENT DOCUMENTS

| | | |
|---|---|---|
| EP | 1 707 127 A1 | 10/2006 |
| WO | WO 2007/002561 A1 | 1/2007 |
| WO | WO 2008/091690 A1 | 7/2008 |

* cited by examiner

KNOTLESS SUTURE CONSTRUCTS

CROSS-REFERENCE TO RELATED APPLICATIONS

This application claims the benefit of U.S. Provisional Application No. 61/510,341 filed Jul. 21, 2011, the entire disclosure of which is incorporated by reference herein.

FIELD OF THE INVENTION

The present invention relates to surgical devices and, in particular, to self-cinching knotless suture constructs.

BACKGROUND OF THE INVENTION

When soft tissue such as a ligament or a tendon becomes detached from a bone, surgery is usually required to reattach or reconstruct the tissue. Often, a tissue graft is attached to the bone to facilitate regrowth and permanent attachment. Techniques and devices that have been developed generally involve tying the soft tissue with suture to an anchor or a hole provided in the bone tissue. Knotless suture anchors, such as the two piece Arthrex PushLock® anchor, disclosed in U.S. Pat. No. 7,329,272, have been developed to facilitate tissue fixation to bone.

It would be desirable to provide a knotless suture construct which has a design that allows tensioning and retensioning of the construct as necessary and upon insertion into bone. Also needed is a knotless suture construct that has the ability to be passed around tissue using standard techniques and then be fixed and tensioned in a straightforward manner. Also needed are methods that easily create self-cinching knotless constructs.

SUMMARY OF THE INVENTION

The present invention provides knotless suture constructs for fixation of soft tissue to bone with the ability to tension/retension the suture construct. The constructs have the ability to be passed around or through tissue using standard techniques and be fixed and tensioned in a straightforward manner. The construct is passed over the tissue to be repaired, then the fixed ends are fixed into bone, and tension is applied to the remaining tensioning ends resulting in a shorter loop length.

The knotless suture constructs of the present invention are self-cinching constructs with at least one splice area, a turning loop (turning eyelet), a fixed end and a tensioning limb. The eyelet is fixed and is formed from the suture splice by either splicing or knotting, or by other known methods in the art. The eyelet is configured to redirect the tensioning of the construct (the force of tensioning).

These and other features and advantages of the invention will be more apparent from the following detailed description that is provided in connection with the accompanying drawings and illustrated exemplary embodiments of the invention.

DETAILED DESCRIPTION OF THE PREFERRED EMBODIMENTS

Figure 1:
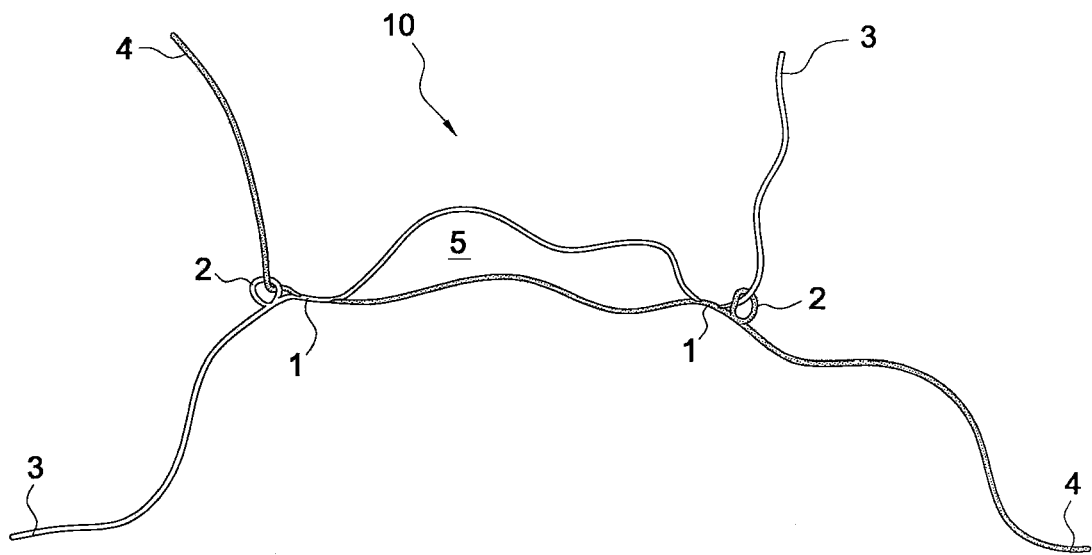
FIG. 1 illustrates a top view of a self-cinching suture knotless construct according to an exemplary embodiment of the present invention.

The present invention provides surgical systems and methods for knotless ligament repair and fixation, such as fixation of soft tissue to bone. The suture construct of the present invention is a suture knotless construct with flexible strands that are self-cinching. The flexible strands may be flexible suture strands, suture tapes, nitinol strands, or high-strength sutures with or without cores, such as ultrahigh molecular weight polyethylene (UHMWPE) suture or FiberWire® suture, among many others.

The knotless suture construct of the present invention is a self-cinching construct with at least one splice area, a turning loop (turning eyelet), a fixed end and a tensioning limb. The eyelet is fixed and is formed from the suture splice by either splicing or knotting, or by other known methods in the art. The eyelet is configured to redirect the tensioning of the construct (the force of tensioning). The knotless constructs may be secured into bone (tissue) with any fixation device which may be any anchor-type device, implants, screws, posts, buttons, or any device that allows attachment/fixation of the knotless construct to tissue.

In one embodiment, the construct has two splice areas, two turning loops, two fixed ends and two tensioning limbs. The construct is passed over the tissue to be repaired and then the fixed ends are fixed into bone. Tension is applied to the tensioning limbs, to result in a shorter loop length. The construct may be secured with one or multiple fixation devices (for example, implants or anchors such as PushLock® anchors).

In another embodiment, the construct is a bridging construct that has a slidable loop, a splice, a turning loop (eyelet), a fixed end with a bridge area and a tensioning limb. The slidable loop of the construct is fixed with a fixation device (for example, a medial PushLock® anchor). The fixed end is passed through or around the tissue to be fixated. Bridge area is fixed with another fixation device (for example, a lateral SwiveLock® anchor) such that the turning loop (eyelet) is just above the bone. Tensioning the tensioning limb causes the construct to tighten against tissue and the splice holds the repair without knots.

In yet another embodiment, the construct has a splice, one turning loop (eyelet), two free ends and a tensioning limb. The two free ends are passed around the tissue to be repaired and then fixed in bone with two fixation devices (for example, PushLock® anchors or SwiveLock® anchors, or combination of the PushLock® and SwiveLock® anchors). The eyelet rests above the bone and redirects the tensioning limb. The free end for tensioning (the tensioning limb) causes the construct to tighten against the tissue and the splice holds the repair without knots.

Referring now to the drawings, where like elements are designated by like reference numerals, FIGS. 1-10 illustrate exemplary self-cinching knotless constructs 10, 20, 30, 40 of the present invention that are provided with various splice areas, fixed ends, tensioning ends (limbs) and turning loops (eyelets). FIGS. 11-16 illustrate subsequent steps of a method of tissue repair with the self-cinching knotless constructs of the present invention. Although the exemplary methods will be described below with reference to fixation devices in the form of particular knotless anchors (having a distal eyelet), the invention is not limited to these embodiments and contemplates fixation of the knotless constructs with any fixation element other than anchors, such as implants, screws, posts, buttons, or a button or a loop on the end that goes around a post, for example.

FIG. 1 illustrates self-cinching suture knotless construct 10 of the present invention provided with two splice areas 1, two turning loops (eyelets) 2, two fixed ends 3 and two tensioning limbs 4. The construct 10 is passed over or through the tissue to be repaired and then fixed ends 3 are fixed into bone using suture anchors. Tension is applied to the tensioning limbs 4, to result in a shorter loop length. The construct may be secured with one or two fixation devices (for example, anchors such as PushLock® anchors and/or SwiveLock® anchors, or any other fixation element), as described in more detail below.

The turning loops or eyelets 2 have a fixed perimeter and are formed in the flexible strands (suture strands) by splicing, or knotting, or by other known methods in the art. The perimeter of the two eyelets 2 may be similar or different. In an exemplary embodiment only, at least one of the eyelets 2 is formed into the suture strand by splicing in a manner similar to that for the formation of the loops of a FiberChain, as described and detailed in U.S. Pat. No. 7,981,140 issued on Jul. 19, 2011 (entitled "Knotless Fixation of Tissue to Bone with Suture Chain"), the entire disclosure of which is incorporated by reference in its entirety herewith. As detailed in U.S. Pat. No. 7,981,140, the loop or "link" can be formed first by "piercing" or "lacing" an end of the suture through a standing part of the suture, to form an initial suture "intersection" in a first direction (for example, in the x-y direction), and then locking the suture intersection by lacing the end through the suture intersection in a second direction (for example, in the z direction), piercing both strands at the center of the initial junction, and pulling the strands tight. The eyelets 2 are configured to redirect the tensioning of the construct (the force of tensioning).

Splice areas 1 and loop 5 are formed—at least in part—in a manner similar to the suture splices used in adjustable suture button/loop construct described in U.S. Patent Application Publication Nos. 2010/0256677 and 2010/0268273, the disclosures of which are incorporated by reference herein (and sold by Arthrex under the tradename ACL TightRope™).

Figure 2:
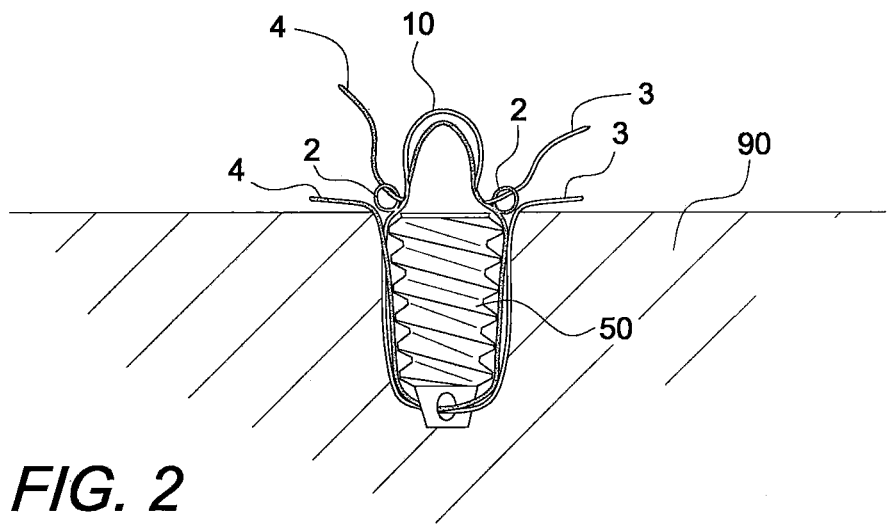
FIG. 2 illustrates the self-cinching suture knotless construct of FIG. 1 secured in bone with one fixation device.
Figure 3:
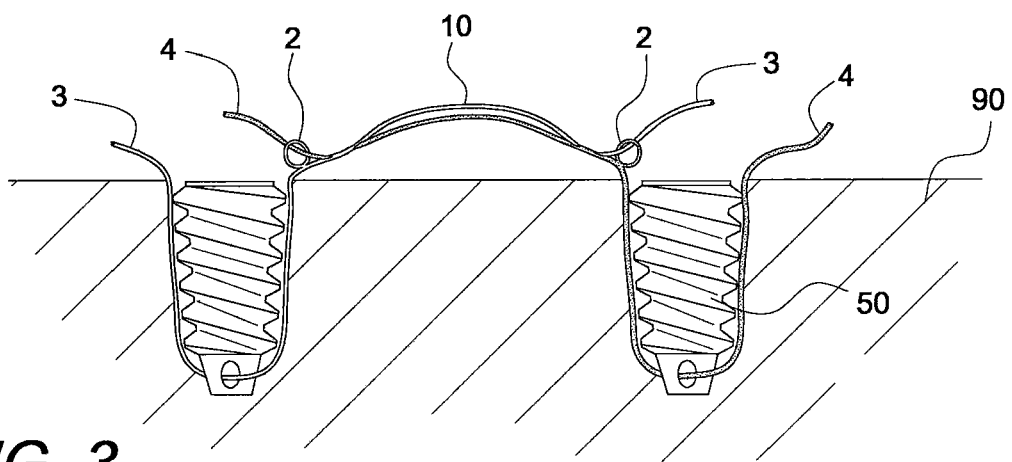
FIG. 3 illustrates the self-cinching suture knotless construct of FIG. 1 secured in bone with two fixation devices.

FIG. 2 illustrates construct 10 secured in bone 90 with one fixation device 50 (for example, a PushLock® anchor 50 or a SwiveLock® anchor 50). FIG. 3 illustrates construct 10 secured in bone 40 with two fixation devices 50 (for example, PushLock® and/or SwiveLock® anchors). In both FIGS. 2 and 3, turning loops (eyelets) 2 are located just above or slightly below the bone 40 to permit easy sliding/tensioning of the constructs.

Figure 4:
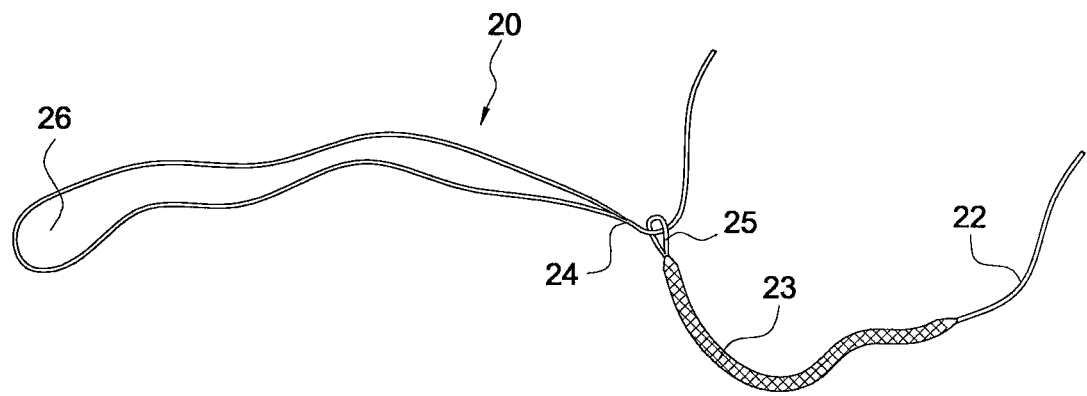
FIG. 4 illustrates a top view of a self-cinching suture knotless construct according to another exemplary embodiment of the present invention.
Figure 5:
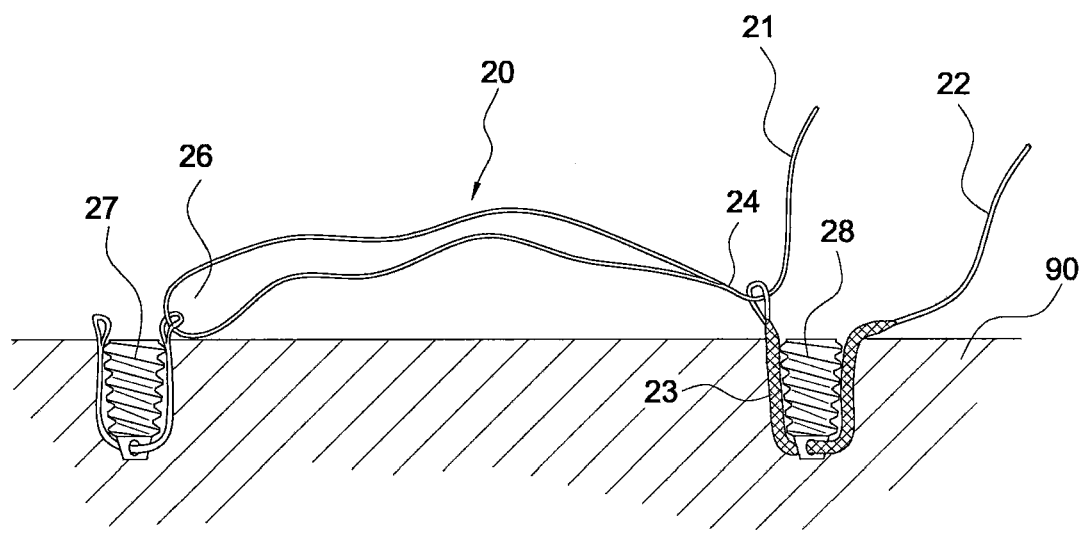
FIG. 5 illustrates the self-cinching suture knotless construct of FIG. 4 secured in bone with two fixation devices.

FIG. 4 illustrates self-cinching suture knotless construct 20 according to another exemplary embodiment of the present invention. In this embodiment, the construct is a "bridging knotless construct" that has a loop 26 which is slidable and flexible and has an adjustable perimeter (length), a bridge 23 (bridge region 23), a splice 24, a turning loop (eyelet) 25, a fixed end 22 connected to the bridge area 23 and a tensioning limb 21. The slidable loop 26 of the construct is fixed with a fixation device 27 (for example, a medial PushLock® anchor). However, any push-in or screw-in anchor with a distal eyelet can be used for these constructs. The fixed end 22 is passed through or around the tissue to be fixated. Bridge area 23 is fixed with another fixation device 28 (for example, a lateral SwiveLock® anchor), as shown in FIG. 5, such that the turning loop (eyelet) 25 is just above the bone 90 or slightly below the bone 90. As long as the eyelet is not wedged against the anchor and the bone, the eyelet can be below the bone. Tensioning the tensioning limb 21 causes the construct 20 to tighten against tissue (shortens the length of the flexible, slidable loop 26) and the splice 24 holds the repair without knots.

Bridge 23 may be formed of suture, reinforced suture, or suture tape. As shown in FIGS. 4 and 5, bridge area 23 may be provided with a width and/or diameter greater than the width and/or diameter of the remaining structures of the construct 20. For example, bridge 23 may be a suture tape with a width greater than that of fixed end 22.

FIG. 5 illustrates the self-cinching suture knotless construct 20 of FIG. 4 secured in bone 90 with two fixation devices 27, 28. The turning loop (eyelet) 25 is formed in a manner similar to that for the formation of eyelets 2 of the first embodiment shown in FIGS. 1-3. Splice 24 (which holds the repair without requiring knots) is formed in a manner similar to that for the formation of splices 1 of FIGS. 1-3.

Construct 20 may be employed in soft tissue repairs such as double row soft tissue repairs, for example, the Suture-Bridge™ tendon repair technique developed by Arthrex, Inc., and disclosed in U.S. Patent Publication No. 2007/0191849, the disclosure of which is herein incorporated by reference in its entirety. As detailed in U.S. Patent Publication No. 2007/0191849, a medial row is provided with a plurality of medial anchors (pre-loaded with constructs 20), the suture limbs from the medial row anchors are passed through or around tissue to be fixated, and then the limbs are secured on a lateral row with a plurality of lateral anchors to complete the repair.

Figure 7:
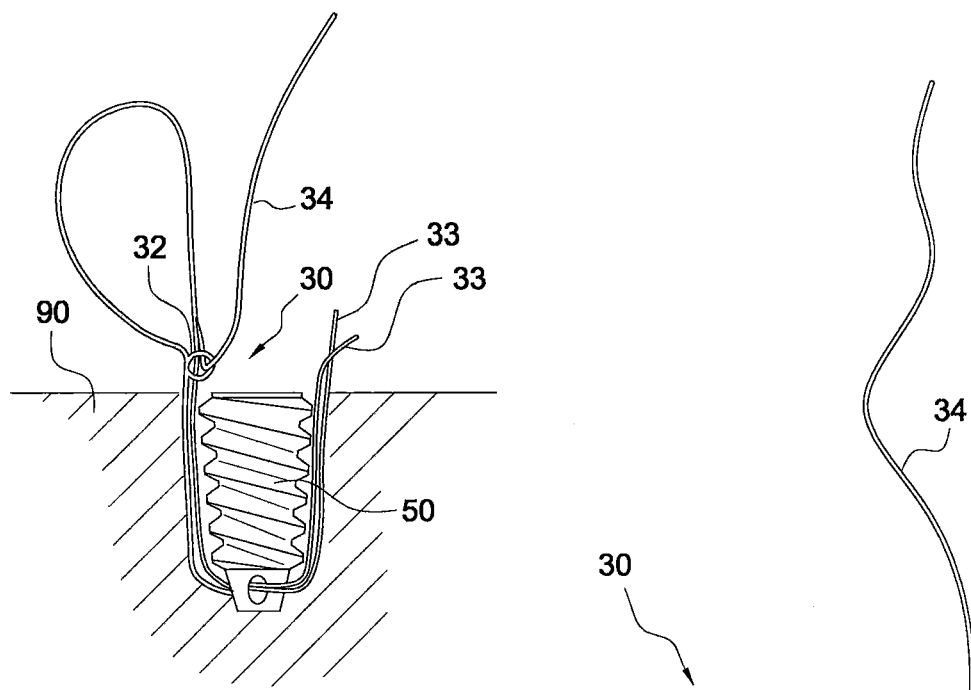
FIG. 7 illustrates the self-cinching suture knotless construct of FIG. 6 secured in bone with one fixation device.
Figure 6:
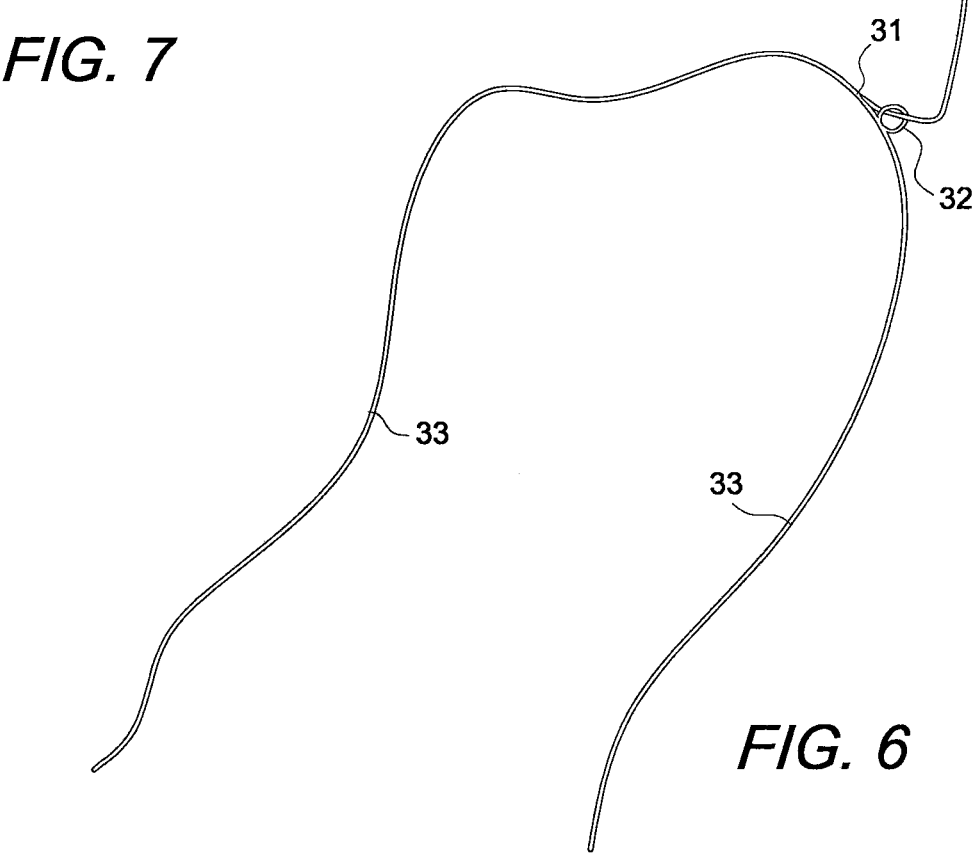
FIG. 6 illustrates a top view of a self-cinching suture knotless construct according to yet another exemplary embodiment of the present invention.

FIGS. 6 and 7 illustrate self-cinching suture knotless construct 30 according to yet another exemplary embodiment of the present invention. The construct is similar to the ones described above but differs in that this construct is provided with a splice area 31, one turning loop (eyelet) 32, two free ends 33 and a tensioning limb 34. The two free ends 33 are passed around the tissue to be repaired and then fixed in bone 90 with a fixation device 50 (for example, a PushLock® anchor or a SwiveLock® anchor), as shown in FIG. 7. Like in the previously-described embodiments, the flexible eyelet 32 (with a fixed length and perimeter) rests above the bone and redirects the tensioning limb 34. The free end 34 for tensioning (the tensioning limb) causes the construct to tighten against the tissue and the splice 31 holds the repair without knots. Turning loop (eyelet) 32 and splice 31 are similar to eyelets 2, 25 and splices 1, 24, respectively, of the previously-described embodiments.

FIG. 7 illustrates the self-cinching suture knotless construct 30 of FIG. 6 secured in bone 90 with fixation device 50. Fixation device 50 may be a SwiveLock® anchor or a PushLock® anchor, or any fixation device provided with a distal eyelet that allows threading (pre-loading) of the knotless construct through the distal eyelet.

Figure 8:
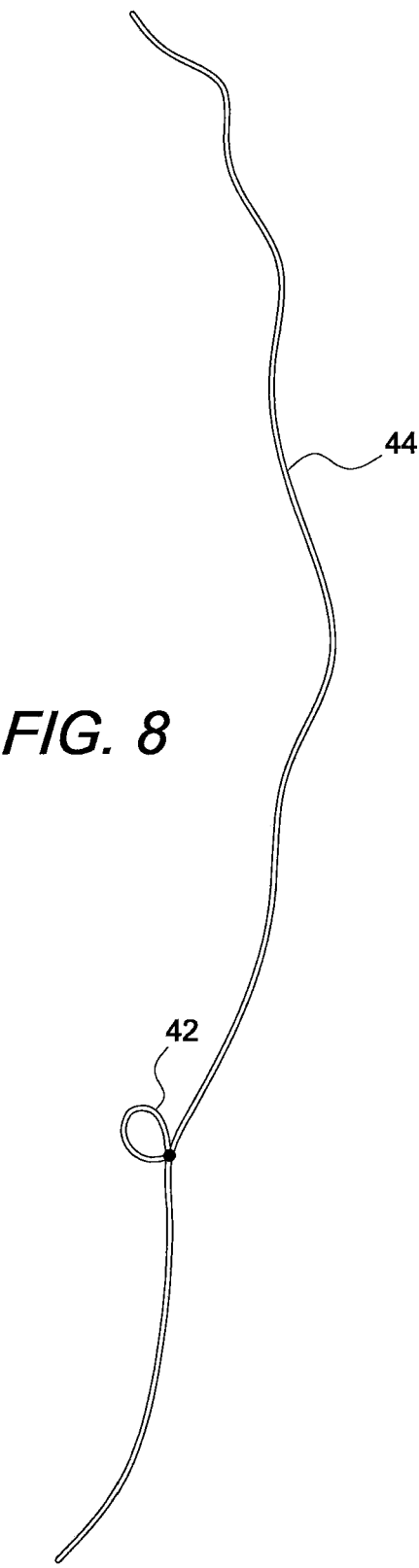
FIGS. 8 and 9 illustrate subsequent steps of a method of forming a suture knotless construct of the present invention.
Figure 9:
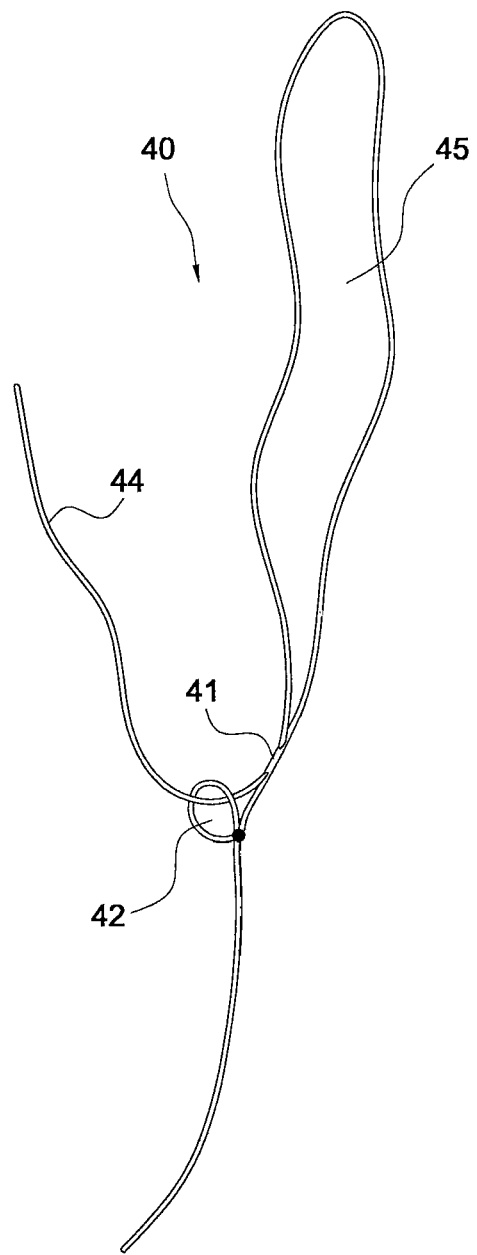

FIGS. 8 and 9 illustrate subsequent steps of forming knotless construct 40 with loop 42 created into the suture splice

41. As in the previously-described embodiments, the eyelet 42 is fixed (i.e., the perimeter of the loop/eyelet is constant and fixed) and is formed in the suture by either splicing (like the loop of a FiberChain) or knotting, or by other known methods in the art. The flexible eyelet 42 is configured to redirect the tensioning of the construct (the force of tensioning). The construct of FIG. 9 acts like a Chinese Finger Trap (TightRope area). Flexible loop 45 has an adjustable length and perimeter and allows tensioning of the final construct.

Suture constructs 10, 20, 30, 40 described above may be employed for knotless tissue repairs, such as fixation of soft tissue to bone. In an exemplary embodiment only, a pilot hole is created in bone by employing a punch or a drill, for example. After the pilot hole is created and the punch or drill is removed, the suture construct 10, 20, 30, 40 is loaded through an eyelet of a knotless suture anchor (which is loaded onto a driver, for example, a standard hand driver). The anchor is positioned on the driver, and the anchor with driver is inserted into the prepared pilot hole by hand. For a push-in anchor, a mallet may be used to advance the implant into the hole. The mallet is used for push-in anchors but could also use screw-in anchors. Once the anchor is advanced into the pilot hole, the driver handle is pulled straight off the anchor. Tensioning/retensioning of the knotless suture construct may be achieved by pulling on the free end 4, 21, 34, 44 to tension the construct, as necessary and as desired.

Figure 10:
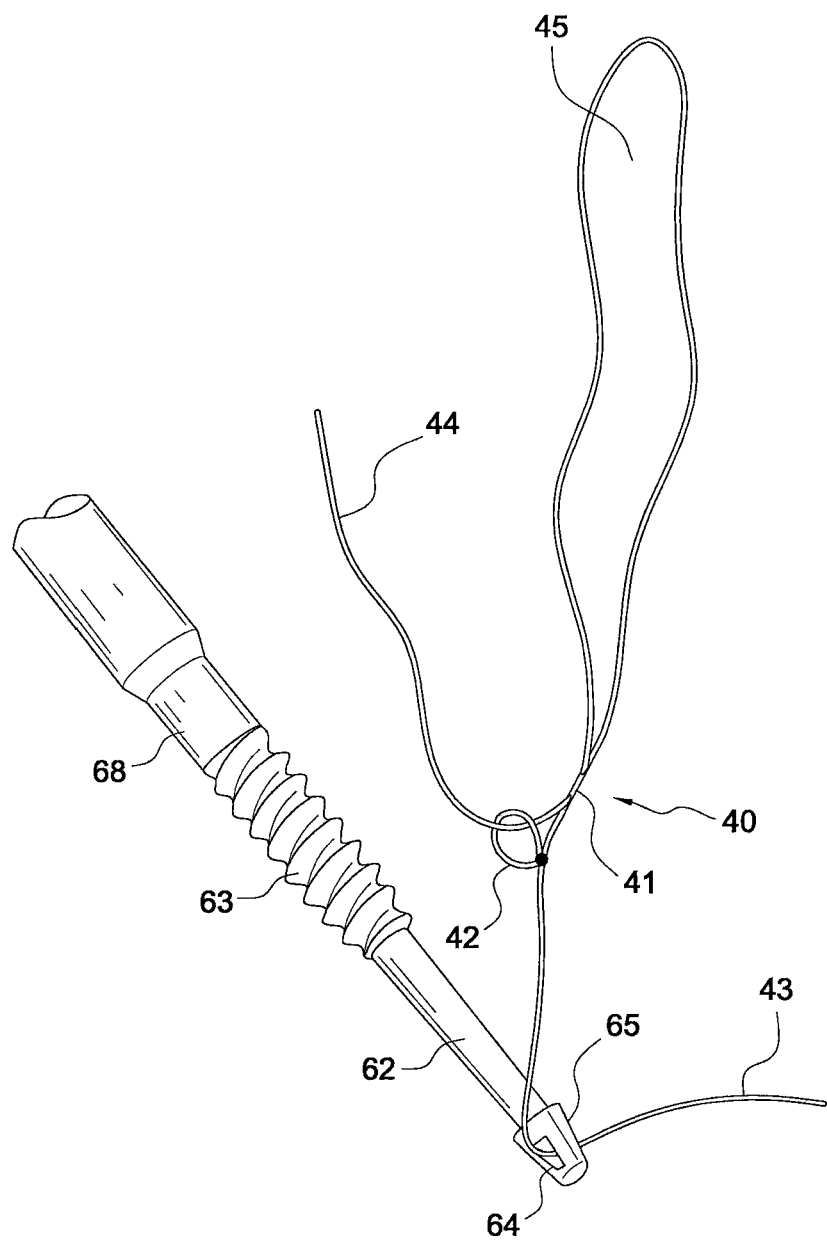
FIG. 10 illustrates the suture knotless construct of FIG. 9 threaded (pre-loaded) through a knotless fixation device.

FIG. 10 illustrates knotless suturing construct 40 threaded through a knotless fixation device 62 such as an Arthrex PushLock® anchor (as disclosed and described in U.S. Pat. No. 7,329,272, the disclosure of which is incorporated by reference in its entirety) or an Arthrex SwiveLock® anchor, disclosed in U.S. Patent Application Publication No. 2008/0004659, the disclosure of which is incorporated by reference in its entirety (shown in FIG. 10). The fixation device 62 comprises an anchor body (or screw) 63 and a distal eyelet 64 at tip 65.

Anchor body 63 may be a screw, such as a cannulated interference screw, that is inserted over the cannulated shaft of the driver 68 and, during use, is advanced and fully seated on the driver tip. Tip 66 is configured to rotate or swivel relative to the shaft and anchor body 63. Tip 66 and anchor body 63 may be configured to experience a snap fit when the two pieces forming the SwiveLock® C anchor 62 engage during installation (i.e., when the threaded anchor body 63 is inserted by rotational insertion to engage the anchor tip 66 and secure the suture anchor in bone).

Construct 40 is pre-loaded (manufactured) on the fixation device 62 (i.e., the knotless construct 40 is pre-loaded through eyelet 64 of the knotless fixation device 62 (SwiveLock® anchor 62)). As described in more detail below, the fixation device 62 with the pre-loaded knotless construct 40 is first inserted into a bone socket or tunnel. The fixed ends of the suture of the construct are passed around or through tissue and then fixed with a PushLock® or SwiveLock® anchor. The fixed eyelet is used to redirect the tensioning suture. The free ends of the construct (the tensioning limbs) are used to tension the final construct. The free ends may be employed further for tissue fixation, for example, may be individually threaded through additional eyelets of additional fixation devices and may be inserted in additional pilot holes (with additional fixation devices) to complete the suture repair system.

FIGS. 11-16 illustrate an exemplary method of tissue repair for rotator cuff 80 with the exemplary knotless construct of FIGS. 8-10. Knotless construct 40 may be employed in an exemplary SutureBridge™ tendon repair technique (a double row soft tissue repair), developed by Arthrex, Inc., and disclosed in U.S. Patent Publication No. 2007/0191849, the disclosure of which is herein incorporated by reference.

Figure 11:
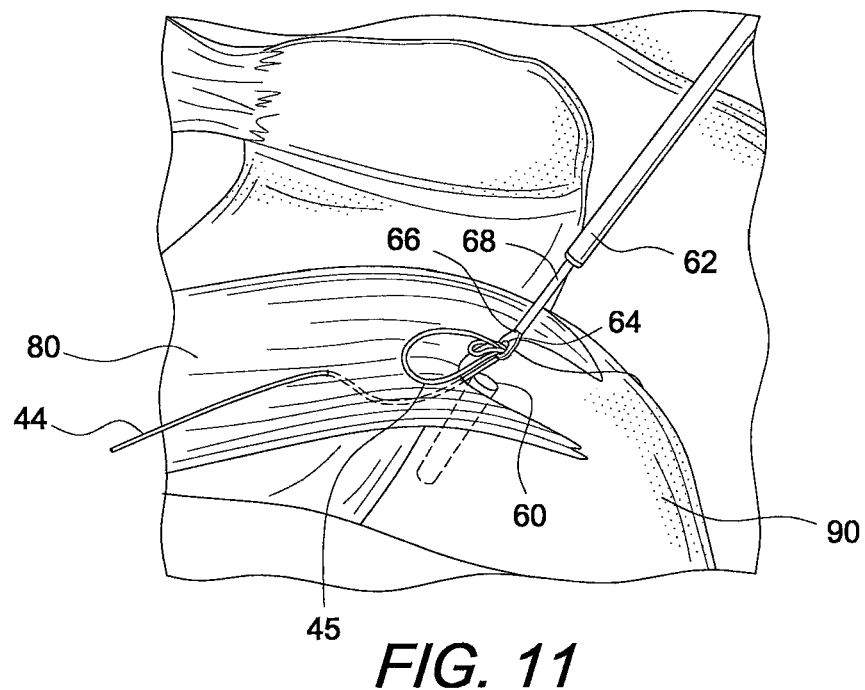
FIGS. 11-16 illustrate subsequent steps of a double row soft tissue repair (arthroscopic rotator cuff repair) with the suturing construct of FIG. 9, and according to an exemplary embodiment of the present invention.

As shown in FIG. 11, the distal tip 66 of the knotless fixation device 62 (with the pre-loaded construct 40) is brought to the edge of pilot hole 60. The fixed end of the knotless construct may be first passed through the rotator cuff 80 to be fixated so that the turning loop (eyelet) 42 is just above the bone (or slightly below the bone). As long as the eyelet is not wedged against the anchor and the bone, the eyelet can be also below the bone.

The driver 68 is then completely advanced into the pilot hole 60 until the anchor body or screw 63 contacts the bone and the ends of the suture construct are fixed within hole 60 by anchor body or screw 63 (as shown in FIG. 7, for example, with fixation device 50) and the fixed eyelet 42 is located just above the bone 90 (FIG. 12) to permit sliding/tensioning.

The driver is rotated in a clockwise direction, for example, to complete insertion. A mallet may be employed to impact the anchor body 63 into the pilot hole 60 until the anchor body is flush with the humerus. The driver 68 is then turned counterclockwise to disengage the eyelet 64 (within pilot hole 60) from the driver shaft. The steps described above are subsequently repeated for the second knotless fixation device 62 (for example, a second SwiveLock® anchor) with another pre-loaded construct 40.

Figure 13:
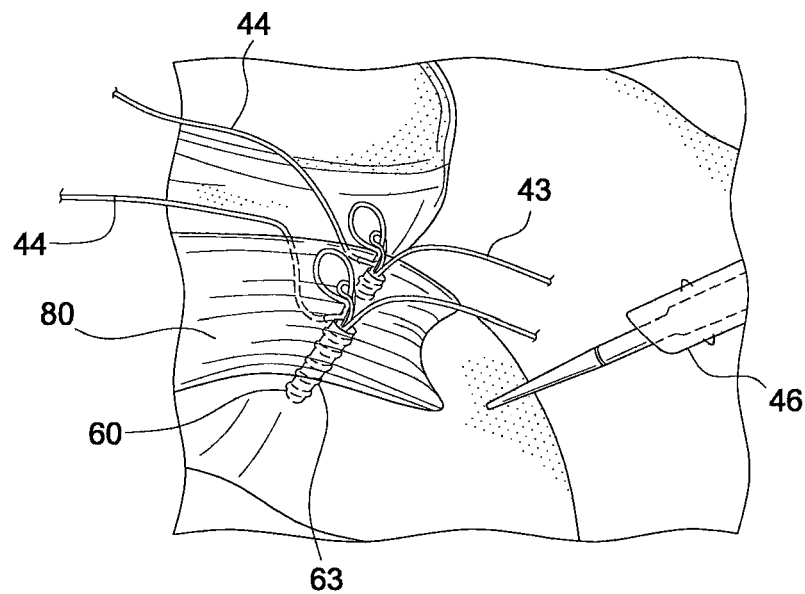
Figure 14:
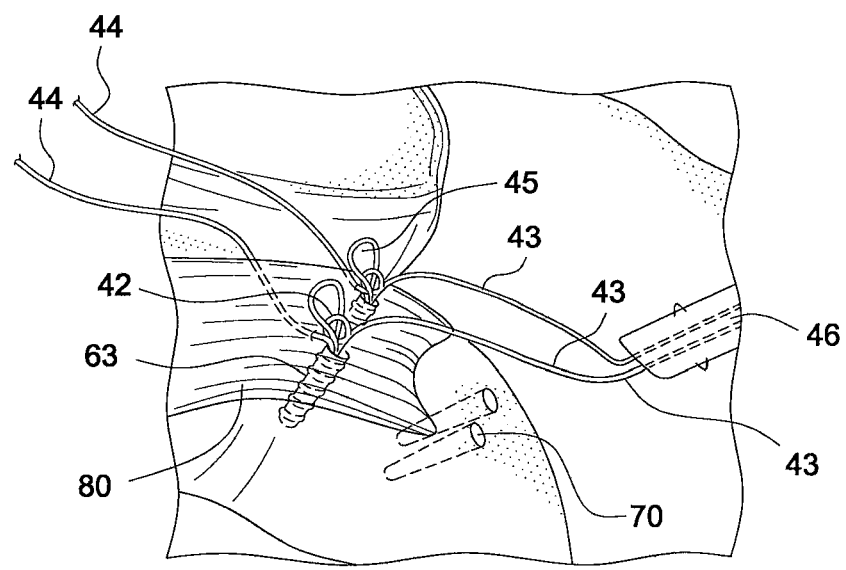
Figure 15:
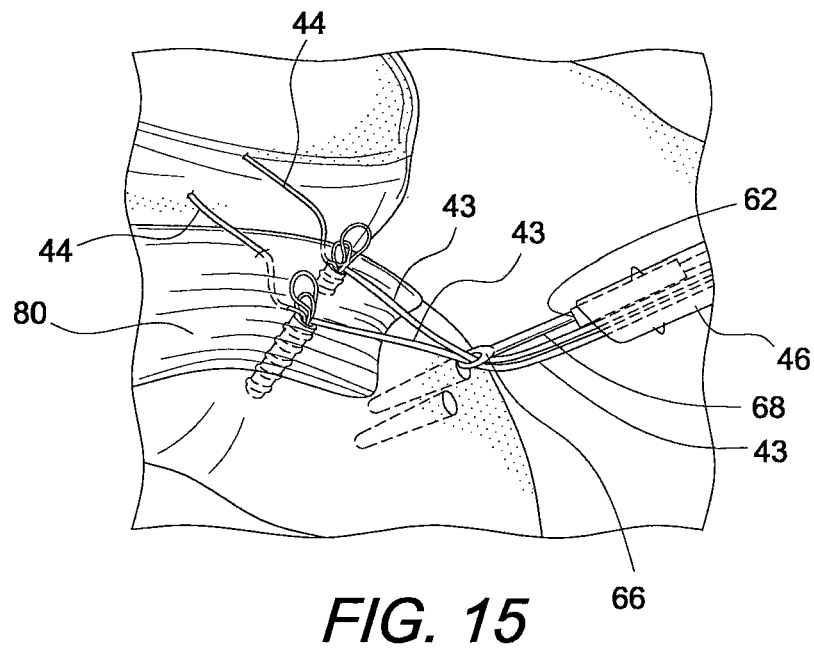
Figure 16:
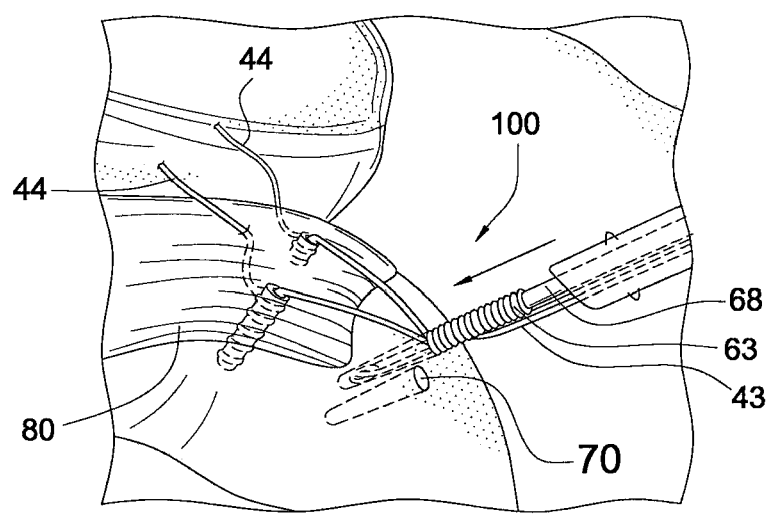

FIG. 13 illustrates two knotless fixation devices 62 with two suturing constructs 40 having eyelets 42 above the bone 90 and ends 43 for additional tissue fixation.

Figure 12:
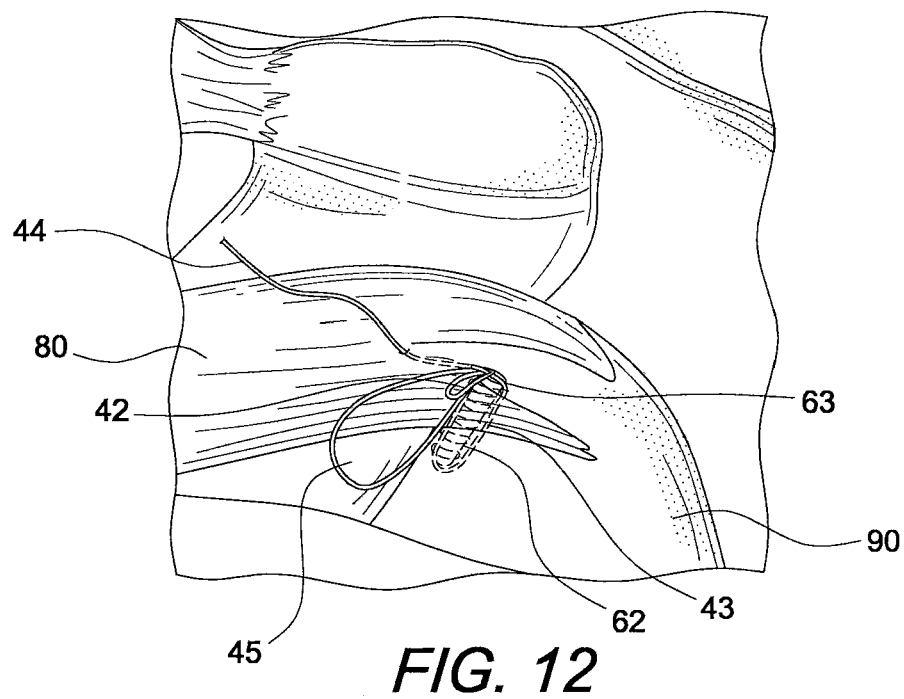

Each of the ends 43 of the suture may be employed further for tissue fixation, for example, each of the two ends may be threaded through additional eyelets of additional fixation devices and may be inserted in additional pilot holes (with additional fixation devices) to complete various suture repairs of the present invention. In an exemplary embodiment only, each end 43 is retrieved and then loaded through another fixation device (for example, a PushLock® anchor) and inserted within pilot holes 70 (FIGS. 14-16) of a lateral row of the suture repair 100 (FIG. 12). Alternatively, each tails 43 may be inserted into a separate prepared lateral bone sockets 70 until the anchor body contacts the bone. Tension is adjusted. Criss-cross suturing pattern 100 (FIG. 16) is completed. Tensioning/retensioning of the knotless suture construct may be achieved by pulling on the free end to tension the construct, as necessary and as desired.

The knotless suture constructs and systems of the present invention are used in conjunction with knotless anchors, for example, swivel and/or screw-in suture anchors and/or push-in suture anchors (such as an Arthrex SwiveLock® anchor, disclosed in U.S. Patent Application Publication No. 2008/0004659 or a PushLock® anchor, as disclosed in U.S. Pat. No. 7,329,272).

The fixation devices 27, 28, 50, 62 may be also any anchors, implants or screws (such as interference screws or tenodesis screws) or any fixation element that allows attachment/fixation of the knotless suture construct to bone. The fixation devices may be also in the form of screws or buttons or posts, for example, in the form of a button or a loop at the end that goes around a post. The fixation devices/implants may have various sizes (various diameters and/or lengths) and may be formed of biocompatible materials such as PEEK, biocomposite materials, metals and/or metal alloys, or combination of such materials, among others.

At least one of flexible strands 3, 4, 21, 22, 33, 34, 44 may be a high-strength suture, such as an ultrahigh molecular weight polyethylene (UHMWPE) suture which is the preferred material as this material allows easy splicing. Alternatively, the high strength suture may be a FiberWire® suture, which is disclosed and claimed in U.S. Pat. No. 6,716,234, the entire disclosure of which is incorporated herein by reference. FiberWire® suture is formed of an advanced, high-strength fiber material, namely ultrahigh molecular weight polyethylene (UHMWPE), sold under the tradenames Spectra (Honeywell) and Dyneema (DSM), braided with at least one other fiber, natural or synthetic, to form lengths of suture material. The preferred FiberWire® suture includes a core within a hollow braided construct, the core being a twisted yarn of UHMWPE.

The flexible strands of the present invention may be also provided in the form of a suture tape (such as the FiberTape® disclosed in U.S. Patent Publication No. 2005/0192631, the disclosure of which is herein incorporated by reference), or a combination of suture strand and suture tape (as shown in FIGS. 4 and 5, wherein region 23 may be a FiberTape® region). The strands may also formed of a stiff material, or combination of stiff and flexible materials, depending on the intended application. The strands may be also coated and/or provided in different colors. The knotless anchors of the present invention can be used with any type of flexible material or suture that forms a splice and a loop.

The knotless suture constructs also include sutures that are spliced—at least in part—in a manner similar to an Arthrex ACL TightRope®, such as disclosed in U.S. Patent Application Publication Nos. 2010/0256677 and 2010/0268273, the disclosures of which are incorporated by reference herein.

Although the present invention has been described in relation to particular embodiments thereof, many other variations and modifications and other uses will become apparent to those skilled in the art. Therefore, the present invention is to be limited not by the specific disclosure herein, but only by the appended claims.

What is claimed as new and desired to be protected by Letters Patent of the United States is:

1. A method of tissue fixation, comprising:
   providing a fixation device having a surgical construct pre-loaded onto the fixation device, the surgical construct comprising a flexible strand with a fixed end and a tensioning end; at least one flexible turning loop or eyelet formed on the flexible strand, the flexible turning loop or eyelet having a fixed perimeter; a slidable loop having an adjustable perimeter; and at least one splice adjacent the flexible turning loop or eyelet, the at least one splice being formed in the flexible strand and having a hollow opening for passage of the flexible strand, the surgical construct being threaded through an eyelet of the fixation device, the flexible loop redirecting tensioning of the surgical construct;
   securing the fixation device with the pre-loaded surgical construct into a bone socket so that at least a portion of the fixed end of the flexible strand is secured into the bone socket;
   passing the fixed end of the surgical construct through or around tissue to be repaired at a surgical site; and
   pulling the tensioning end to adjust the length of the surgical construct and to fixate tissue, while the flexible turning loop or eyelet redirects tensioning of the surgical construct.

2. The method of claim 1, wherein the flexible turning loop or eyelet is formed by splicing or knotting the flexible strand.

3. The method of claim 1, further comprising the step of threading the tensioning end of the flexible strand through an eyelet of another fixation device.

4. The method of claim 1, wherein the fixation device further comprises an anchor body and the eyelet.

5. The method of claim 1, wherein the surgical site is part of a shoulder, a knee, a hip, or an elbow.

\* \* \* \* \*